United States Patent
Okamoto et al.

(10) Patent No.: US 10,703,693 B2
(45) Date of Patent: *Jul. 7, 2020

(54) METHOD FOR PRODUCING 1,3-DICHLORO-3,3-DIFLUOROPROPENE

(71) Applicant: CENTRAL GLASS COMPANY, LIMITED, Yamaguchi (JP)

(72) Inventors: Masamune Okamoto, Saitama (JP); Kohei Sumida, Saitama (JP); Kei Matsunaga, Saitama (JP); Yoshio Nishiguchi, Saitama (JP); Satoru Okamoto, Saitama (JP)

(73) Assignee: CENTRAL GLASS COMPANY, LIMITED, Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/572,867

(22) Filed: Sep. 17, 2019

(65) Prior Publication Data

US 2020/0010388 A1 Jan. 9, 2020

Related U.S. Application Data

(63) Continuation of application No. PCT/JP2018/021834, filed on Jun. 7, 2018.

(30) Foreign Application Priority Data

Jun. 30, 2017 (JP) .................. 2017-128292

(51) Int. Cl.
*C07C 17/25* (2006.01)
*C07C 17/20* (2006.01)
*C07C 21/18* (2006.01)
*B01J 27/12* (2006.01)

(52) U.S. Cl.
CPC .......... *C07C 17/208* (2013.01); *B01J 27/12* (2013.01); *C07C 17/206* (2013.01); *C07C 17/25* (2013.01); *C07C 21/18* (2013.01)

(58) Field of Classification Search
None
See application file for complete search history.

(56) References Cited

U.S. PATENT DOCUMENTS

| 9,994,502 | B1* | 6/2018 | Merkel | ............... C07C 17/383 |
| 2012/0059199 | A1* | 3/2012 | Pokrovski | ............ C01B 7/0706 570/155 |
| 2016/0332936 | A1* | 11/2016 | Wang | ..................... C07C 17/25 |
| 2018/0148394 | A1 | 5/2018 | Pigamo et al. | |

FOREIGN PATENT DOCUMENTS

| JP | H10-309464 A | 11/1998 |
| JP | 2012-020992 A | 2/2012 |
| WO | 2016/189214 A1 | 12/2016 |

OTHER PUBLICATIONS

International Search Report dated Jul. 24, 2018 and Written Opinion of the International Searching Authority for corresponding International application No. PCT/JP2018/021834, with English translation of the International Search Report.
Written Opinion issued for corresponding International Patent Application No. PCT/JP2018/021834 dated Jul. 24, 2018, along with an English translation.

* cited by examiner

*Primary Examiner* — Medhanit W Bahta
(74) *Attorney, Agent, or Firm* — Hauptman Ham, LLP

(57) ABSTRACT

A manufacturing method of 1-chloro-3,3,3-trifluoropropene (1233zd) is provided. This manufacturing method includes a reaction in which a halogenated hydrocarbon compound having a carbon number of 3 and represented by a general formula (1) is heated:

$$CF_aCl_{3-a}-CH_2-CHF_bCl_{2-b} \quad (1)$$

In the formula, a is an integer from 0 to 2, b is 1 or 2 when a=0, b is 0 or 1 when a=1, and b is 0 when a=2.

14 Claims, No Drawings

METHOD FOR PRODUCING 1,3-DICHLORO-3,3-DIFLUOROPROPENE

CROSS REFERENCE TO RELATED APPLICATION

This application is based upon and claims the benefit of priority from the prior Japanese Patent Application No. 2017-128292, filed on Jun. 30, 2017. Further, this application is a continuation Application of International Application No. PCT/JP2018/021834, filed on Jun. 7, 2018. Both of the priority documents are hereby incorporated by reference in their entireties.

FIELD

An embodiment of the present invention relates to a manufacturing method of 1,3-dichloro-3,3-difluoropropene (hereinafter, also referred to as 1232zd).

BACKGROUND

The compound 1232zd is a known compound. This compound is one kind of hydrofluoroolefin (HFO) with a low global warming potential coefficient (GWP) and has been expected as an operation medium for a thermal cycle.

As a manufacturing method of 1232zd, a method is known where 1,1,3,3,3-pentachloropropane (hereinafter, also referred to as 240fa) is fluorinated in a gas phase in the presence of hydrogen fluoride, for example (Japanese Patent Application Publication No. 2012-20992). A method is also known where 1,1,3,3-tetrachloropropene (hereinafter, also referred to as 1230za) is chlorofluorinated with chlorine and hydrogen fluoride in a gas phase (Japanese Patent Application Publication No. H10-309464). Although 1232zd can be obtained in a high yield by each method, use of a more than stoichiometric amount of hydrogen fluoride is required. The use of a large amount of hydrogen fluoride increases the risk of an accident resulting in injury or death and puts pressure on risk management when leaked.

An industrially applicable manufacturing method for manufacturing 1232zd is still being demanded.

SUMMARY

An object of an embodiment of the present invention is to provide an efficient (and industrially applicable) manufacturing method of 1,3-dichloro-3,3-difluoropropene (1232zd).

Diligent study was made by the inventors to solve the aforementioned problem. As a result, it was found that 1232zd can be manufactured by heating a halogenated hydrocarbon compound having a carbon number of 3, through which the present invention was made. The present invention is realized by the embodiments described below.

Namely, an embodiment of the present invention is a manufacturing method of 1,3-dichloro-3,3-difluoropropene, and the manufacturing method includes a reaction in which a halogenated hydrocarbon compound having a carbon number of 3 and represented by a general formula (1) is heated.

(1)

In the formula, a is an integer from 0 to 2, b is 1 or 2 when a=0, b is 0 or 1 when a=1, and b is 0 when a=2.

This reaction may be carried out in a gas phase. Moreover, this reaction may be conducted in the presence or in the absence of a metal catalyst. The metal catalyst may include at least one kind of metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten. The metal catalyst may be selected from an oxide of the metal, an oxyhalide of the metal, or a halide of the metal. The metal catalyst may also include at least a fluorine atom.

The metal catalyst may be a supported catalyst or a non-supported catalyst. A support for the supported catalyst may be selected from carbon, an oxide of the metal, an oxyhalide of the metal, or a halide of the metal.

This reaction may be carried out in the presence or in the absence of a filler. The filler may include at least one kind of material selected from carbon, plastics, ceramics, and a metal.

This reaction may be carried out in the presence of at least one kind of compound selected from 1,3,3,3-tetrafluoropropene, 1,1,3,3-tetrafluoropropene, and 1,1,1,3,3-pentafluoropropane.

In this reaction, 1,1,3,3-tetrachloropropene, 1,3,3-trichloro-3-fluoropropene, or 1-chloro-3,3,3-trifluoropropene may be formed in addition to 1,3-dichloro-3,3-difluoropropene.

This reaction may be carried out at a temperature from 100° C. to 500° C.

This reaction may be conducted in a liquid phase. Moreover, this reaction may be carried out in the presence of a base.

In this reaction, hydrogen fluoride may not be substantially supplied.

According to an embodiment of the present invention, it is possible to provide an efficient (and industrially applicable) manufacturing method of 1,3-dichloro-3,3-difluoropropene (1232zd).

DESCRIPTION OF EMBODIMENTS

Hereinafter, each embodiment of the present invention is explained. The embodiments of the present invention should not be interpreted only within the description of the embodiments and examples shown below.

A method according to an embodiment of the present invention includes a reaction in which a halogenated hydrocarbon compound having a carbon number of 3 and represented by a general formula (1) is heated.

(1)

In the general formula (1), a is an integer from 0 to 2, b is 1 or 2 when a=0, b is 0 or 1 when a=1, and b is 0 when a=2.

As the halogenated hydrocarbon compound having a carbon number of 3 and represented by the general formula (1), 1,1,3,3-tetrachloro-1-fluoropropane (hereinafter, also referred to as 241fa), 1,1,1,3-tetrachloro-3-fluoropropane (hereinafter, also referred to as 241fb, 1,3,3-trichloro-1,1-difluoropropane (hereinafter, also referred to as 242fa), 1,1,3-trichloro-1,3-difluoropropane (hereinafter, also referred to as 242fb), and 1,1,1-trichloro-3,3-difluoropropane (hereinafter, also referred to as 242fc) are specifically represented. These compounds may be separately used, or a plurality of these compounds may be simultaneously used. Among these compounds, 242fa, 242fb, and 242fc are particularly preferred because 1232zd is preferentially formed. These compounds are known compounds which can be manufactured by the known methods.

This reaction may be carried out in a gas phase or a liquid phase.

This reaction may be carried out in a gas phase in the presence or in the absence of a catalyst. A metal catalyst may be used as the catalyst. The metal catalyst specifically includes at least one kind of metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten. A compound of the aforementioned metal is preferred, and an oxide, an oxyhalide, and a halide of the metals described above are more preferable. The halogen of the halide may be any of iodine, bromine, chlorine, and fluorine. The metal catalyst is further preferred to be a partially halogenated compound or fully halogenated compound of the aforementioned metals, and a partially fluorinated compound or a fully fluorinated compound of the aforementioned metals is particularly preferred.

The metal catalyst may be a supported catalyst or a non-supported catalyst. The support in the case of the supported catalyst is not particularly limited, and it is preferred to employ carbon as well as an oxide, an oxyhalide (preferably an oxyfluoride), and a halide (a fluoride) of the metals described above, and the like. Among these supports, activated carbon or an oxide, an oxyhalide (an oxyfluoride is particularly preferred), and a halide (a fluoride is particularly preferred) of at least one kind of metal selected from aluminum, chromium, zirconium, and titanium is particularly preferred. In the case of the supported catalyst, the substance supported by the support is the compound of the aforementioned metals and is supported on the support as a fluoride, a chloride, a fluorochloride, an oxyfluoride, an oxychloride, an oxyfluorohalide, or a nitrate of the metals, or the like. Such metal compounds may be separately supported, or more than two kinds of metal compounds may be concurrently supported. Chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper(II) chloride, zinc(II) chloride, lanthanum nitrate, tin tetrachloride, and the like can be specifically used as the supported substance.

The metal catalyst is preferred to be used in this reaction after being subjected to a fluorinating treatment. A method of the fluorinating treatment is not particularly limited, and the fluorinating treatment is generally performed by contacting a fluorinating agent such as hydrogen fluoride, a fluorinated hydrocarbon, and a fluorinated and chlorinated hydrocarbon with the metal catalyst. The temperature of the fluorinating treatment is not particularly limited, and the fluorinating treatment is performed at 200° C. or higher, for example. There is no upper limit to the temperature of the fluorinating treatment, and the fluorinating treatment is practically preferred to be conducted at 600° C. or lower.

The present reaction may be performed in the presence or in the absence of a filler. As such a filler, carbon such as activated carbon, heat-resistant plastics, ceramics, and a 0-valent metal such as stainless steel are represented. Among them, activated carbon is particularly preferred. This reaction may be carried out in the presence of at least one kind of filler selected from carbon, heat-resistant plastics, and ceramics.

In the present reaction process, the heating temperature (reaction temperature) is not particularly limited as long as the target compound can be formed. The present reaction may be conducted at 100° C. to 150° C., the reaction temperature is preferred to be 150° C. to 430° C., and 150° C. to 380° C. is particularly preferred. Alternatively, the present reaction may be carried out in a liquid phase at 0° C. to 100° C., and the reaction temperature of 20° C. to 90° C. is more preferable in this case.

In the present reaction, the reaction pressure is not particularly limited, and the present reaction may be conducted at a reduced pressure, at a normal pressure (an atmospheric pressure), or under pressure. The present reaction may be conducted at 0.01 MPaG to 10 MPaG (i.e., a gage pressure. The same is applied below.), a pressure of 0.01 MPaG to 1 MPaG is preferred, and an atmospheric pressure is more preferable. It is not economically preferred when the pressure exceeds 10 MPaG because the cost for a pressure-proof design of a reaction vessel is increased.

In the case of a gas-phase flow system, productivity is often discussed using a value (second) obtained by dividing a volume A (mL) of a reaction zone by a raw-material supplying rate B (mL/sec), and this value is called a contact time. When a catalyst is added to the reaction zone, the apparent volume (mL) of the catalyst is recognized as A described above. The value of B means "a volume of a raw gas supplied to a reaction vessel every second" and, in this case, is calculated from a molar number of the raw gas, a pressure, and a temperature under an assumption that the raw gas is an ideal gas.

Determination of the contact time depends on the raw material used in the present reaction, the reaction temperature, the kind of the catalyst, and the like. Thus, it is desirable to appropriately adjust the supply rate of the raw material in view of the raw material, the temperature of the reaction apparatus, and the kind of the catalyst in order to optimize the contact time.

In the present reaction, the contact time may be 0.1 second to 300 seconds, the contact time of 5 seconds to 150 seconds is preferred, and 10 seconds to 100 seconds is more preferable. The contact time may be appropriately modified according to the reaction pressure.

In the case where the present reaction is conducted in a liquid phase, it is preferable to conduct the reaction in the presence of a base. As such a base, an organic base such as an alkylamine, a pyridine, an aniline, a guanidine, a lutidine, a morpholine, a piperidine, a pyrrolidine, a pyrimidine, and a pyridazine, ammonia, and an inorganic base such as an alkaline metal alkoxide, a carbonate of an alkaline metal, a carbonate of an alkaline earth metal, a hydroxide of an alkaline metal, and a hydroxide of an alkaline earth metal are represented. One kind of base may be used, or a two or more kinds of base may be combined and used. The amount of the base which is used is not limited, 1 mol to 10 moles of the base with respect to the halogenated hydrocarbon compound having a carbon number of 3 and represented by the general formula (1) may be used, 1 mole to 4 moles are preferred, and 1 mole to 3 moles are more preferable.

When the present reaction is carried out in a liquid phase, the reaction may be conducted in the presence of a solvent. One kind of solvent may be used, or two or more kinds of solvent may be combined and used. If necessary, one kind or more than one kind of phase-transfer catalyst may be employed.

In the reaction according to the present invention, the reaction vessel is not particularly limited, and the use of a gas-phase reaction vessel or a liquid-phase reaction vessel is preferred, depending on the reaction type. The gas-phase reaction vessel formed of a material with thermal resistance and acid resistance is preferred, and a reaction vessel formed of stainless steel, Hastelloy™, Monel™, platinum, nickel, carbon, a fluorine resin, or a material lined with these materials is exemplified. However, the material is not limited thereto. The liquid-phase reaction vessel formed of a material with thermal resistance and acid resistance is preferred, and a reaction vessel formed of stainless steel, Hastelloy™, Monel™, platinum, nickel, carbon, a fluorine resin, glass, or a material lined with these materials is exemplified. However, the material is not limited thereto.

The present reaction may be conducted in the presence of at least one kind of fluorocarbon compound selected from 1,3,3,3-tetrafluoropropene (hereinafter, also referred to as 1234ze), 1,1,3,3-tetrafluoropropene (hereinafter, also referred to as 1234zc), and 1,1,1,3,3-pentafluoropropane (hereinafter, also referred to as 245fa).

In the present reaction, although hydrogen fluoride may be supplied to the reaction vessel or may not be supplied, it is preferred not to supply hydrogen fluoride. In the present reaction, the halogenated hydrocarbon compound having a carbon number of 3 and represented by the general formula (1) may be heated without substantially supplying hydrogen fluoride to the reaction vessel.

The fluorocarbon compound may be independently used, or two or more kinds of fluorocarbon compound may be concurrently used. Among them, 245fa and 1234ze are preferred. Note that 1234ze may be a cis form (hereinafter, also referred to as 1234ze(Z)), a trans form (hereinafter, also referred to as 1234ze(E)), or a mixture thereof. These compounds are known compounds which can be manufactured by the known methods.

The amount of the fluorocarbon compound which is used is not particularly limited. It is preferred to use 5 mol % to 500 mol % of the fluorocarbon compound with respect to the halogenated hydrocarbon compound having a carbon number of 3 and represented by the general formula (1), and 10 mol % to 300 mol % is particularly preferred.

In the present reaction process, an inert gas such as nitrogen, argon, and helium or an oxidizing gas such as chlorine, oxygen, and air may be supplied to the reaction vessel in view of maintenance and an increase of the activity of the metal catalyst and the like. Such a gas may be independently supplied to the reaction vessel or may be supplied to the reaction vessel together with the halogenated hydrocarbon compound having a carbon number of 3 and represented by the general formula (1) and the fluorocarbon compound. The gas may be separately used or may be a mixed gas. The amount of the gas supplied to the reaction vessel is not limited. It is preferred to use 0.0001 mol % to 200 mol % of the gas with respect to the halogenated hydrocarbon compound having a carbon number of 3 and represented by the general formula (1), the 0.001 mol % to 100 mol % is more preferable, and 0.1 mol % to 10 mol % is particularly preferred.

The procedure of the method according to the present embodiment is shown. The halogenated hydrocarbon compound having a carbon number of 3 and represented by the general formula (1) is introduced to the reaction vessel and is heated under the aforementioned conditions. If necessary, the fluorocarbon compound is also introduced to the reaction vessel. These raw materials are introduced to the reaction vessel via different flow paths or the same flow path. It is preferred that the catalyst and the filler be disposed in the reaction vessel in advance. When the reaction is carried out in a gas phase, these raw materials are preferred to be in a gas state when introduced to the reaction vessel. If necessary, these raw materials are gasified with a vaporizer and then introduced to the reaction vessel. After that, the reaction is conducted in the reaction vessel under the aforementioned conditions.

A method for purifying the target compound from the reaction products obtained by the present reaction is not particularly limited. If necessary, a removing treatment of a chlorine component or an acid component which may be included in the reaction products may be carried out. Moisture may also be removed by a dehydration treatment and the like, and the dehydration treatment may be conducted with the removing treatment of a chlorine component or an acid component. For example, after the reaction products are allowed to flow through a cooled condenser to be condensed, washed with water and/or an alkaline solution to remove a chlorine component, an acid component, and the like, and dried with a desiccant such as zeolite or activated carbon, the target compound with high purity can be obtained by a distillation operation.

When unreacted raw materials or biproducts other than the target compound are included in the reaction products, they can be independently separated and recovered from the reaction products by a purification operation such as distillation. The separated halogenated hydrocarbon compound having a carbon number of 3 and represented by the general formula (1) and the fluorocarbon compound can be reused as the raw materials of the present reaction and may also be subjected to a variety of usages. Similar to these compounds, the biproducts other than the target compound may be supplied to the present reaction, if necessary, or may be employed in a variety of usages.

According to the present embodiment, 1,3-dichloro-3,3-difluoropropene (1232zd) may be obtained as a cis form (hereinafter, also referred to as 1232zd(Z)), a trans form (hereinafter, also referred to as 1232zd(E)), or a mixture thereof, and these cis/trans isomers can be individually separated by a purification operation such as distillation. The mixture of the cis/trans isomers of 1232zd or the separated isomers may each be employed in a variety of usages.

In the present embodiment, the present reaction may result in 1,3,3-trichloro-3-fluoropropene (hereinafter, also referred to as 1231zd). This 1231zd may be obtained as a cis form (hereinafter, also referred to as 1231zd(Z)), a trans form (hereinafter, also referred to as 1231zd(E)), or a mixture thereof, and these cis/trans isomers may be separated from each other by a purification operation such as distillation. The mixture of the cis/trans isomers of 1231zd or the separated isomers may each be employed in a variety of usages. The compound 1231zd is a type of hydrofluoroolefin (HFO) with a low global warming potential coefficient (GWP) and is expected as an alternative fluorocarbon.

In the present embodiment, the present reaction may result in 1,1,3,3-tetrachloropropene (1230za). This 1230za may be employed in a variety of usages. If necessary, 1230za with high purity can be obtained by conducting a purification operation. The compound 1230za is useful as a raw material for manufacturing a variety of hydrofluoroolefins (HFO) and the like.

In the present embodiment, the present reaction may result in 1-chloro-3,3,3-trifluoropropene (hereinafter, also referred to as 1233zd) as a cis form (hereinafter, also referred to as 1233zd(Z)), a trans form (hereinafter, also referred to as 1233zd(E)), or a mixture thereof. If necessary, 1233zd, 1233zd(Z), and 1233zd(E) with high purity can be obtained by conducting a purification operation. The compound 1233zd is useful as a detergent, a coolant, and the like.

EXAMPLES

Hereinafter, an embodiment according to the present invention is explained in detail using Examples. The embodiments of the present invention are not limited to the Examples.

In the present specification, the term FID % means an area percentage of a chromatogram obtained by a gas chromatography analysis using an FID as a detector.

Preparation Example 1. Preparation of Fluorinated Activated Almina

Activated alumina (KHS-46 manufactured by Sumitomo Chemical Co., Ltd, particle size of 4 to 6 mm and a specific surface area of 155 m$^2$/g), 300 g, was weighed out, and powder adhered on its surface was washed out with water. To the washed alumina was added 1150 g of 10 wt % hydrofluoric acid, and the mixture was stirred and then kept standing for 4 hours. After washing with water, the activated alumina was filtered, dried at a normal temperature overnight, and then dried in an electric furnace at 200° C. for 2 hours. Into a reaction tube made of stainless steel (SUS 316) and having an internal diameter of 1 inch and a length of 40 cm was added 150 mL of the dried alumina, and the temperature of the reaction tube was increased to 200° C. in the electric furnace while allowing nitrogen to flow therethrough at a flow rate of 150 cc/sec and then allowing hydrogen fluoride to flow therethrough at a flow rate of 0.1 g/min together with nitrogen. Since the temperature increases as the hydrogen fluoride treatment proceeds, the flow rates of nitrogen and hydrogen fluoride were adjusted to prevent the inner temperature from exceeding 400° C. When the heat generation was completed, the flow rate of nitrogen was dropped to 30 cc/sec, the set temperature of the electric furnace was increased by 50° C. every 30 minutes to a final temperature of 400° C., and then this state was maintained for two hours. The activated alumina subjected to the fluorinating treatment (hereinafter, also referred to as a catalyst 1) was prepared in this way.

Preparation Example 2. Preparation of Fluorinated Chromium-Supporting Almina Catalyst A 20 wt % aqueous solution of chromium chloride was added to an Erlenmeyer flask, and 100 mL of the activated alumina subjected to the fluorinating treatment and prepared in the Preparation Example 1 was soaked and kept therein for 3 hours. This alumina was filtered and dried at 70° C. under a reduced pressure using a rotary evaporator. Into a cylinder-shaped reaction tube made of stainless steel (SUS 316), having an internal diameter of 1 inch and a length of 40 cm, and equipped with an electric furnace was charged 100 mL of this chromium-supporting alumina, and the temperature was increased to 200° C. while allowing nitrogen to flow therethrough. When no more water outflow was observed, nitrogen gas and hydrogen fluoride (HF) were simultaneously supplied at flow rates of 150 cc/sec and 0.1 g/sec, respectively, and the flow rates of nitrogen and hydrogen fluoride were adjusted so that the inner temperature does not exceed 400° C. When the hot spot caused by the fluorination of the charged chromium-supporting alumina reached an outlet terminal of the reaction tube, the flow rate of nitrogen was reduced to 30 cc/sec, the set temperature of the electric furnace was increased by 50° C. every 30 minutes to the final temperature of 400° C., and then this state was maintained for 2 hours. The chromium-supporting alumina subjected to the fluorinating treatment (hereinafter, also referred to as a catalyst 2) was prepared in this way.

Preparation Example 3. Preparation of Fluorinated Chromium-Supporting Activated Carbon A 20 wt % aqueous solution of chromium chloride was added to an Erlenmeyer flask, and 100 mL of activated carbon was soaked and maintained therein for 3 hours. This activated carbon was filtered and dried at 70° C. under a reduced pressure using a rotary evaporator. Into a cylinder-shaped reaction tube made of stainless steel (SUS 316), having an internal diameter of 1 inch and a length of 40 cm, and equipped with an electric furnace was charged 100 mL of this chromium-supporting activated carbon, and the temperature was increased to 200° C. while allowing nitrogen to flow therethrough. When no more water outflow was observed, nitrogen gas and hydrogen fluoride were simultaneously supplied at flow rates of 150 cc/sec and 0.1 g/sec, respectively, and the flow rates of nitrogen and hydrogen fluoride were adjusted so that the inner temperature does not exceed 400° C. When the hot spot caused by the fluorination of the charged chromium-supporting activated carbon reached an outlet terminal of the reaction tube, the flow rate of nitrogen was reduced to 30 cc/sec, the set temperature of the electric furnace was increased by 50° C. every 30 minutes to the final temperature of 400° C., and then this state was maintained for 2 hours. The chromium-supporting activated carbon subjected to the fluorinating treatment (hereinafter, also referred to as a catalyst 3) was prepared in this way.

Example 1-1

Into a cylinder-shaped reaction tube made of stainless steel (SUS 316), having an internal diameter of 1 inch and a length of 40 cm, and equipped with an electric furnace was charged 50 mL of activated carbon, and the internal temperature of the reaction tube was increased to 200° C. while allowing nitrogen gas to flow therethrough at a flow rate of approximately 30 cc/min. After that, the supply of nitrogen was stopped, and vaporized 1,1,3,3-tetrachloro-1-fluoropropane (241fa, purity of 98.2 FID %, the same is applied below) was introduced into the reaction tube (contact time of 120 seconds). When the flow rate became stable, 500 mL of a water trap cooled with ice water was disposed at an outlet of the reaction tube, by which the organic substances were recovered and a by-produced acid component was absorbed for approximately 100 minutes. The gas passing through the water trap was recovered by a dry ice trap disposed next to the water trap, and the recovered materials in the water trap and the dry ice trap were mixed. The composition of the organic substances obtained by removing an acid from the recovered materials was analyzed using gas chromatography. The result is shown in Table 1.

Example 1-2

The same operations were carried out as those of the Example 1-1 except that the contact time was 31 seconds and the internal temperature of the reaction tube was set to 250° C.

Example 1-3

The same operations were carried out as those of the Example 1-1 except that 1,3,3-trichloro-1,1-difluoropropane (242fa, purity of 96.7 FID %, the same is applied below) was introduced (contact time of 86 seconds) instead of 1,1,3,3-tetrachloro-1-fluoropropane (241fa) and the internal temperature of the reaction tube was set to 250° C.

Example 1-4

The same operations were carried out as those of the Example 1-1 except that 241fa and 1,3,3-trichloro-1,1-difluoropropane (242fa) (molar ratio of 241fa/242fa=1/9, contact time of 54 seconds) were introduced instead of 1,1,3,3-tetrachloro-1-fluoropropane (241fa) and the internal temperature of the reaction tube was set to 220° C.

Example 1-5

The same operations were carried out as those of the Example 1-1 except that 1,3,3-trichloro-1,1-difluoropropane (242fa) was introduced (contact time of 65 seconds) instead of 1,1,3,3-tetrachloro-1-fluoropropane (241fa) and the internal temperature of the reaction tube was set to 340° C.

Example 1-6

Into a cylinder-shaped reaction tube made of stainless steel (SUS 316), having an internal diameter of 1 inch and a length of 40 cm, and equipped with an electric furnace was charged 50 mL of the catalyst prepared in the Preparation Example 1, and the internal temperature of the reaction tube was increased to 200° C. while allowing nitrogen gas to flow therethrough at a flow rate of approximately 30 cc/min. After that, the supply of nitrogen was stopped, and vaporized 1,1,3,3-tetrachloro-1-fluoropropane (241fa) and 1,1,1,3,3-pentafluoropropane (245fa, purity of 99.9 FID %, the same is applied below) were introduced into the reaction tube (molar ratio of 241fa/245fa=1/1, contact time of 60 seconds). When the flow rate became stable, 500 mL of a water trap cooled with ice water was disposed at an outlet of the reaction tube, by which the organic substances were recovered and a by-produced acid component was absorbed for approximately 100 minutes. The gas component passing through the water trap was recovered by a dry ice trap disposed next to the water trap, and the recovered materials in the water trap and the dry ice trap were mixed. The composition of the organic substances obtained by removing an acid from the recovered materials was analyzed using gas chromatography. The result is shown in Table 1.

Example 1-7

The same operations were carried out as those of the Example 1-6 except that 1,3,3-trichloro-1,1-difluoropropane (242fa) and 245fa (molar ratio of 242fa/245fa=1/0.5, contact time of 60 seconds) were introduced instead of 1,1,3,3-tetrachloro-1-fluoropropane (241fa) and 1,1,1,3,3-pentafluoropropane (245fa).

Example 1-8

The same operations were carried out as those of the Example 1-7 except that 50 mL of the catalyst prepared in the Preparation Example 2 was charged instead of the catalyst prepared in the Preparation Example 1.

Example 1-9

The same operations were carried out as those of the Example 1-7 except that 50 mL of the catalyst prepared in the Preparation Example 2 was charged instead of the catalyst prepared in the Preparation Example 1 and the internal temperature of the reaction tube was set to 350° C.

Example 1-10

The same operations were carried out as those of the Example 1-7 except that 50 mL of the catalyst prepared in the Preparation Example 3 was charged instead of the catalyst prepared in the Preparation Example 1 and 1,1,1,3-tetrafluoropropene (1234ze, purify of 99.9 FID %) was introduced (molar ratio of 242fa/1234ze=1/1, contact time of 60 seconds) instead of 1,1,1,3,3-pentafluoropropane (245fa).

Example 1-11

The same operations were carried out as those of the Example 1-6 except that 1,1,1,3,3-pentafluoropropane (245fa) was not introduced and the internal temperature of the reaction tube was set to 300° C.

Example 1-12

The same operations were carried out as those of the Example 1-11 except that 1,3,3-trichloro-1,1-difluoropropane (242fa) was introduced instead of 1,1,3,3-tetrachloro-1-fluoropropane (241fa).

The results of the Examples 1-1 to 1-12 are summarized in Table 1. In Table 1, "-" means that no substance was detected.

| Examples | Raw Material 1 | Raw Material 2 | Catalyst | Reaction Temperature [° C.] | Organic Composition [FID %] | | | | | | | | Raw Material 1 |
|---|---|---|---|---|---|---|---|---|---|---|---|---|---|
| | | | | | 1234zeE | 245fa | 1234zeZ | 1233zdE | 1233zdZ | 1232zd | 1231zd | 1230za | |
| 1-1 | 241fa | None | None | 200 | — | — | — | <0.1 | <0.1 | 9.1 | 48 | 20.2 | 12 |
| 1-2 | 241fa | None | None | 250 | — | — | — | <0.1 | <0.1 | 15.7 | 32.5 | 29.3 | 5.0 |
| 1-3 | 242fa | None | None | 250 | — | — | — | 0.8 | 0.2 | 93 | <0.1 | 2.3 | 2.1 |
| 1-4 | 241fa + 242fa | None | None | 220 | — | — | — | 0.8 | 0.2 | 90.1 | 1.2 | 2.4 | 3.1 |
| 1-5 | 242fa | None | None | 340 | — | — | — | 1.3 | 0.4 | 82.1 | 0.9 | 3.0 | 6.6 |
| 1-6 | 241fa | 245fa | Catalyst 1 | 200 | 9 | 15 | 1 | 19.5 | 3 | 1 | 1 | 27 | 22 |
| 1-7 | 242fa | 245fa | Catalyst 1 | 200 | 6.1 | 17 | 1 | 20.5 | 2.6 | 8.1 | <0.1 | 17 | 26.1 |
| 1-8 | 242fa | 245fa | Catalyst 2 | 200 | 0.2 | 30.8 | 0.1 | 25.6 | 3 | 9.8 | <0.1 | 1.3 | 28.5 |
| 1-9 | 242fa | 245fa | Catalyst 2 | 350 | 0.8 | 8.8 | 0.1 | 72.1 | 9.1 | 3.7 | <0.1 | 2.8 | 1.3 |
| 1-10 | 242fa | 1234ze | Catalyst 3 | 200 | 20.1 | 3.8 | 5.5 | 14.1 | 1.6 | 13.1 | <0.1 | 13.9 | 26.2 |

-continued

| Examples | Raw Material 1 | Raw Material 2 | Catalyst | Reaction Temperature [° C.] | Organic Composition [FID %] | | | | | | | | Raw Material 1 |
| | | | | | 1234zeE | 245fa | 1234zeZ | 1233zdE | 1233zdZ | 1232zd | 1231zd | 1230za | |
|---|---|---|---|---|---|---|---|---|---|---|---|---|---|
| 1-11 | 241fa | None | Catalyst 1 | 300 | — | — | — | 31.3 | 3.2 | 2.1 | 0.1 | 63.2 | <0.1 |
| 1-12 | 242fa | None | Catalyst 1 | 300 | — | — | — | 56.1 | 6.1 | 4.2 | <0.1 | 30.3 | 2.5 |

As shown in Table 1, it was confirmed that implementation of an embodiment of the present invention provides the target compound 1232zd from the halogenated hydrocarbon compound, such as 241fa and 242fa, having a carbon number of 3 and represented by the general formula (1).

Example 2-1

A 25 wt % aqueous solution of potassium hydroxide (two equivalents with respect to 242fa) was fed in a three-necked flask equipped with a stirrer, a thermometer, and a dropping funnel and was stirred while being heated at 85° C. Into this aqueous solution was added dropwise 1,3,3-trichloro-1,1-difluoropropane (242fa), and a generated gas was recovered in an ice-cooled trap placed at an outlet of the reaction vessel. When no more gas generation was observed, the reaction was stopped. Analysis of the composition of the obtained organic substances using gas chromatography revealed that 1232zd was 53.3 FID %, and 242fa was 30.1 FID %.

INDUSTRIAL APPLICABILITY

The use of a halogenated hydrocarbon compound, which is readily available and has a carbon number of 3, as a raw material allows a chlorofluoropropene having a low GWP and applicable in a variety of usages to be manufactured in an industrial scale.

What is claimed is:

1. A method for manufacturing 1,3-dichloro-3,3-difluoropropene, the method comprising a reaction in which a halogenated hydrocarbon compound having a carbon number of 3 and represented by a general formula (1) is heated:

$$CF_aCl_{3-a}-CH_2-CHF_bCl_{2-b} \quad (1)$$

wherein the reaction is carried out in the presence of at least one selected from the group consisting of 1,3,3,3-tetrafluoropropene, 1,1,3,3-tetrafluoropropene, and 1,1,1,3,3-pentafluoropropane, and wherein, in the formula, a is an integer from 0 to 2, b is 1 or 2 when a=0, b is 0 or 1 when a=1, and b is 0 when a=2.

2. The method according to claim 1, wherein the reaction is carried out in a gas phase.

3. The method according to claim 1, wherein the reaction is carried out in the presence or in the absence of a metal catalyst.

4. The method according to claim 3, wherein the metal catalyst includes at least one metal selected from the group consisting of aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten.

5. The method according to claim 4, wherein the metal catalyst is an oxide of the metal, an oxyhalide of the metal, or a halide of the metal.

6. The method according to claim 4,
wherein the metal catalyst is a supported catalyst or a non-supported catalyst, and
a support of the supported catalyst is carbon, an oxide of the metal, an oxyhalide of the metal, or a halide of the metal.

7. The method according to claim 3, wherein the metal catalyst includes at least a fluorine atom.

8. The method according to claim 1, wherein the reaction is carried out in the presence or in the absence of a filler.

9. The method according to claim 8, wherein the reaction is carried out in the presence of the filler, and the filler is at least one selected from the group consisting of carbon, plastics, ceramics, and a metal.

10. The method according to claim 1, wherein 1,1,3,3-tetrachloropropene, 1,3,3-trichloro-3-fluoropropene, or 1-chloro-3,3,3-trifluoropropene is formed in addition to 1,3-dichloro-3,3-difluoropropene in the reaction.

11. The method according to claim 1, wherein the reaction is carried out at a temperature from 100° C. to 500° C.

12. The method according to claim 1, wherein the reaction is carried out in a liquid phase.

13. The method according to claim 12, wherein the reaction is carried out in the presence of a base.

14. The method according to claim 1, wherein hydrogen fluoride is not supplied in the reaction.

* * * * *